United States Patent
Cramer Von Clausbruch

(10) Patent No.: US 10,405,952 B2
(45) Date of Patent: Sep. 10, 2019

(54) BLANK FOR PRODUCING A DENTAL PROSTHESIS

(71) Applicant: Ivoclar Vivadent AG, Schaan (LI)

(72) Inventor: Sascha Cramer Von Clausbruch, Mühlacker (DE)

(73) Assignee: Ivoclar Vivadent AG, Schaan (LI)

( * ) Notice: Subject to any disclaimer, the term of this patent is extended or adjusted under 35 U.S.C. 154(b) by 99 days.

(21) Appl. No.: 14/381,302

(22) PCT Filed: Feb. 28, 2013

(86) PCT No.: PCT/EP2013/054049
§ 371 (c)(1),
(2) Date: Aug. 27, 2014

(87) PCT Pub. No.: WO2013/127931
PCT Pub. Date: Sep. 6, 2013

(65) Prior Publication Data
US 2015/0125822 A1 May 7, 2015

(30) Foreign Application Priority Data
Feb. 29, 2012 (DE) .................. 10 2012 203 154

(51) Int. Cl.
*A61C 13/00* (2006.01)
*A61C 8/00* (2006.01)
(Continued)

(52) U.S. Cl.
CPC ........ *A61C 13/0022* (2013.01); *A61C 8/0012* (2013.01); *A61C 13/0006* (2013.01);
(Continued)

(58) Field of Classification Search
CPC . A61C 13/0006; A61C 13/082; A61C 13/083; A61C 13/0012; A61C 13/0022; Y10T 29/49567
(Continued)

(56) References Cited

U.S. PATENT DOCUMENTS 5,151,044 A * 9/1992 Rotsaert ............ A61C 13/0003
428/542.8
5,873,721 A * 2/1999 Willoughby ......... A61C 8/0001
433/172
(Continued)

FOREIGN PATENT DOCUMENTS

DE 19838239 A1 3/2000
DE 10150647 A1 4/2003
(Continued)

OTHER PUBLICATIONS

International Preliminary Report on Patentability of PCT/EP2013/054049, dated Sep. 2, 2014, 7 pages.
(Continued)

*Primary Examiner* — Nicholas D Lucchesi
(74) *Attorney, Agent, or Firm* — Ann M. Knab; Thad McMurray

(57) ABSTRACT

A blank which is provided for producing dental shaped parts such as crowns, bridges, veneers, abutments and the like, already has at least one preform of a dental shaped part, which is available for producing this shaped part.
In particular, the preforms in the blank are prepared by machining of the blank, preferably by cutting, sawing, grinding, drilling and/or milling. The preforms are in particular preforms for single crowns.

27 Claims, 1 Drawing Sheet

Figure 1A:
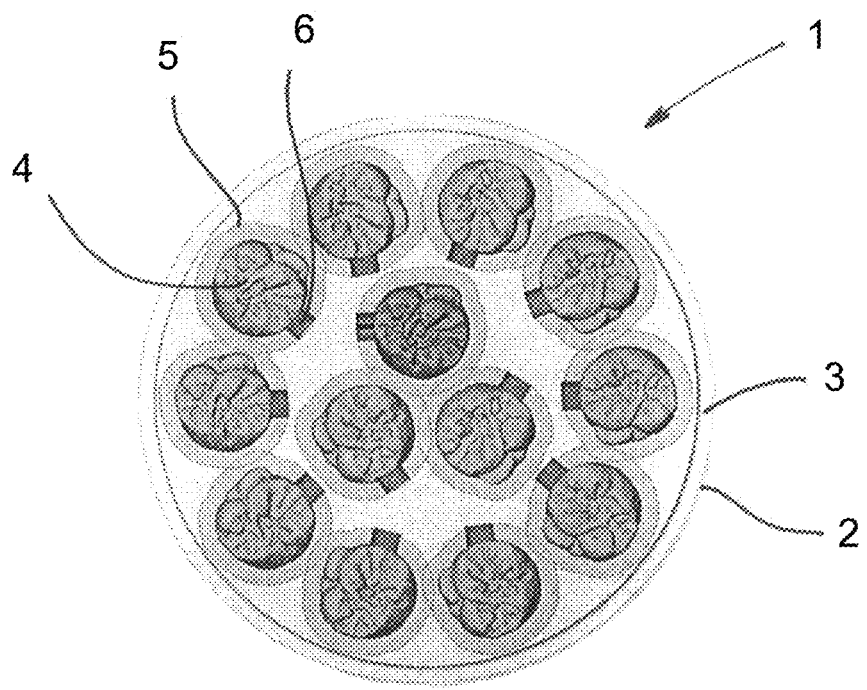

(51) Int. Cl.
*A61C 13/08* (2006.01)
*A61C 13/083* (2006.01)
*A61C 13/09* (2006.01)

(52) U.S. Cl.
CPC .......... *A61C 13/082* (2013.01); *A61C 13/083* (2013.01); *A61C 13/09* (2013.01); *Y10T 29/49567* (2015.01)

(58) Field of Classification Search
USPC ............................... 433/49, 202.1, 223, 229
See application file for complete search history.

(56) References Cited

U.S. PATENT DOCUMENTS

| | | | | |
|---|---|---|---|---|
| 6,660,400 | B1* | 12/2003 | Hintersehr | A61C 13/0003 206/63.5 |
| 6,979,496 | B2* | 12/2005 | Haymann | A61C 13/0022 428/542.8 |
| 6,994,549 | B2* | 2/2006 | Brodkin | A61C 13/0003 264/19 |
| 7,604,759 | B2 | 10/2009 | Gubler et al. | |
| 7,871,268 | B2* | 1/2011 | Touchstone | A61C 13/0004 433/203.1 |
| 8,483,857 | B2* | 7/2013 | Orth | A61C 13/0004 700/118 |
| 8,551,622 | B2* | 10/2013 | Ganley | A61C 13/0022 428/542.2 |
| 8,568,897 | B2* | 10/2013 | Ganley | A61C 13/0022 409/163 |
| 2004/0241614 | A1 | 12/2004 | Goldberg et al. | |
| 2005/0008989 | A1* | 1/2005 | Rothenberger | A61C 13/0022 433/202.1 |
| 2006/0172263 | A1 | 8/2006 | Quadling et al. | |
| 2007/0290385 | A1 | 12/2007 | Holzner et al. | |
| 2009/0181346 | A1 | 7/2009 | Orth | |
| 2009/0275000 | A1* | 11/2009 | Jung | A61C 13/0004 433/223 |
| 2010/0203478 | A1* | 8/2010 | Rubbert | A61C 5/007 433/212.1 |
| 2010/0233658 | A1 | 9/2010 | Ganley et al. | |
| 2010/0285429 | A1* | 11/2010 | Karim | A61C 5/10 433/199.1 |
| 2012/0183921 | A1* | 7/2012 | Karlsson | A61C 5/002 433/49 |
| 2012/0214133 | A1* | 8/2012 | Jung | A61C 8/005 433/174 |
| 2012/0251979 | A1* | 10/2012 | Karim | A61C 8/005 433/201.1 |
| 2013/0316305 | A1* | 11/2013 | Carden | A61K 6/0088 433/202.1 |
| 2013/0330690 | A1* | 12/2013 | Svensson | A61C 5/10 433/219 |
| 2014/0377718 | A1* | 12/2014 | Korten | A61C 13/0022 433/218 |
| 2015/0093719 | A1* | 4/2015 | Beeby | A61C 13/0013 433/202.1 |
| 2015/0093720 | A1* | 4/2015 | Beeby | A61C 13/0022 433/202.1 |
| 2015/0111172 | A1* | 4/2015 | Jung | A61C 13/0003 433/172 |
| 2016/0228222 | A1* | 8/2016 | Rolf | A61C 13/0004 |

FOREIGN PATENT DOCUMENTS

| | | |
|---|---|---|
| DE | 102006021640 B3 | 10/2007 |
| DE | 102006025660 A1 | 12/2007 |
| DE | 102007013065 A1 | 9/2008 |
| DE | 112004000561 B4 | 1/2010 |
| DE | 202010009686 U1 | 9/2010 |
| DE | 102009040909 A1 | 4/2011 |
| EP | 1992302 A1 | 11/2008 |
| JP | H10277059 A | 10/1998 |
| WO | 2011/029615 A1 | 3/2011 |

OTHER PUBLICATIONS

Merriam-Webster Inc., Definition of "preform", Webster's Third New International Dictionary, 1986, p. 1787, USA.

* cited by examiner

BLANK FOR PRODUCING A DENTAL PROSTHESIS

CROSS-REFERENCE TO RELATED APPLICATIONS

This application is a National Stage application of International patent application PCT/EP2013/054049 filed on Feb. 28, 2013, which claims priority to German patent application No. 10 2012 203 154.5 filed on Feb. 29, 2012, the disclosures of which are incorporated herein by reference in their entirety.

The invention relates to a blank for producing dental shaped parts (dental prostheses), such as crowns, bridges, veneers, abutments, among others, as well as a process for producing this blank and a process for producing dental prostheses.

In recent years, dental prostheses made of ceramic materials have become increasingly important. Not only are these materials used, as has already long been known, for veneering frameworks made of metal, but the whole dental prosthesis, for example consisting of framework and veneer, is manufactured from ceramic. In this way, all-ceramic dental prostheses, for example all-ceramic crowns and all-ceramic bridges, are achieved. As ceramic materials the so-called oxide ceramics, and of these in particular zirconium dioxide ($ZrO_2$), are to be particularly emphasized.

In the case of all-ceramic dental prostheses, the frameworks, and also other dental shaped parts, such as veneers, abutments (implant build-up parts) or even whole teeth, are generally machined from a ceramic block, the so-called blank or ingot. This is carried out in particular by milling and/or by drilling, cutting, sawing, grinding and the like.

Among other things, the times within which the corresponding dental shaped parts can be machined from the ceramic block are important in this connection. In order to achieve relatively short processing times with an acceptable tool wear, as a rule unsintered (not sintered) or partially sintered (not finally- or not densely-sintered) ceramic material is therefore used for the mentioned blocks. The sintering shrinkage which inevitably occurs during the necessary dense-sintering of the dental shaped parts must therefore already be taken into account in advance during the design of the dental shaped parts.

The object of the invention is therefore for one thing to further reduce the processing times for producing the dental shaped parts from ceramic blocks. For another, the resulting advantages are also intended to be transferrable to the processing of other materials in dental engineering.

This object is achieved by the blank with the features of claim 1. Preferred embodiments of this blank are to be found in the subclaims which are dependent on claim 1. The process according to the invention for producing the blank or for producing dental prostheses as well as the use according to the invention of the blank is defined in claims 15 to 23.

The wording of all of the claims is hereby incorporated into the content of this description by reference.

By "blank" is meant any body of any geometry from which the corresponding dental shaped parts can be machined, preferably by a mechanical processing such as milling, cutting, sawing, drilling, grinding and the like. Such blanks, which are often also called "ingots", can accordingly be cuboidal, cubic or cylindrical. Any other geometries are also possible, such as for example conical or spherical blanks. In particular cylindrical blanks can preferably be discoidal blanks. By definition a disk is a body, in particular a cylinder, the thickness of which is smaller, in particular substantially smaller, than its radius.

The preform is formed in the blank according to the invention. It is a three-dimensional body which, in terms of its dimensions and/or its shape/design, is approximated or adapted to the dimensions and/or the shape/design of the dental shaped part that is to be produced. As a result, this means that the preparation of the dental shaped part from the blank is facilitated because of the at least partly adapted or anticipated dimensions and/or shapes of the preform.

The preform can only roughly approximate the dimensions and/or the shape of the dental shaped part or at least partly already anticipate these parameters. This will be explained in further detail later in connection with the example and the figures.

It is preferred in the invention if the preform(s) were obtained in the blank by machining. This is preferably carried out by cutting, sawing, grinding, drilling and/or in particular by milling.

In principle, a wide variety of dental shaped parts can be provided as preforms in the blank according to the invention. Thus, it can for example be inlays, onlays, veneers, partial veneers, implant parts, such as abutments, or even bridges or bridge pontics. However, the preforms provided in the blank are preferably provided for preparing (single) crowns from the blank. A wide variety of crowns, such as those for incisal teeth, canine teeth or molar teeth, can be involved here.

It is particularly advantageous if not only one or two preforms, but a plurality of preforms, are present in the blank according to the invention.

The blank can then be exploited to the optimum in terms of space and volume for producing dental shaped parts. It is hereby further preferred if more than five, in particular more than ten, preforms are provided in the blank according to the invention.

The preform or preforms are advantageously connected to the blank by at least one bar or a comparable bridge element. This bar is cut through when the dental shaped part is machined from its corresponding preform.

The bar itself is formed during the production of the corresponding preform, for example by machining, with the result that a stable, but simultaneously easily separable connection between preform and (the rest of the) blank remains. Although it is preferred to provide only one bar between preform and blank, if necessary two or more bars can also be formed. The cross-sectional area of the bar can be designed as required, wherein as a rule a circular cross-sectional area is preferred.

The blank according to the invention is usually cuboidal, cubic or cylindrical.

The blank according to the invention can preferably have the shape of a disk. The preforms were formed, in particular mechanically machined, from this original disk. By "discoidal shape" is meant according to the invention any geometric design of the blank in which the corresponding body has a smaller, in particular much smaller, thickness than the diameter of the blank. The diameter of the disk is in particular at least 20 mm. The term "discoidal" is intended to express that the invention is not limited to round, i.e. substantially circular, disks, but can also include deviations from the circular shape. These include for example blanks with oval cross-sectional surfaces, for example elliptical cross-sectional surfaces. Other cross-sectional surfaces with at least partially curved circumferential lines are also intended to be comprised, such as for example disks the outer circumference of which is similar to the outer contour of a horseshoe.

The discoidal blank according to the invention has in particular the shape of a substantially circular disk. In all discoidal blanks, including the circular disks, the diameter is at least 20 mm. Diameters of 50 mm are further preferred. Diameters of more than 80 mm, in particular of 100 mm, are advantageously also possible.

In the case of disks that deviate in the shape of the diameter from the circular shape, by diameter is meant the largest distance between two points which lie on the outer circumference of the disk.

In the case of all discoidal blanks, in particular in the case of the last-mentioned disks which are substantially circular, the thickness of the disk is in particular greater than 5 mm. Thicknesses of the disks of between 5 mm and 30 mm are still further preferred.

In a further embodiment, the blank according to the invention can have at least one holding means for clamping the blank during its processing to form a dental shaped part. This holding means thus serves to (as a rule reversibly) hold or secure the blank in a corresponding processing machine, for example a milling machine.

The at least one holding means is preferably formed directly on the blank, for example also via a fixing such as a bonding, or shaped, such as for example via at least one recess, in particular groove, running at least partially on the outer circumference of the blank.

The blank according to the invention can in principle consist of or be manufactured from all materials which are used in dental engineering for such blanks (ingots). For all these materials, the processing times are reduced by the preforms provided in the blank. Materials can also be used the use of which was previously not possible or not economical due to the long times for processing from a solid material (without preforms).

Advantageously, the blank is manufactured from a plastic material as is usually employed for such blanks. These can be for example synthetic waxes or also acrylic polymers, for example based on methyl methacrylate. In such cases, the blank preferably consists of PMMA (polymethyl methacrylate) or PU (polyurethane).

In a preferred embodiment, the plastic material is a composite material which contains at least partly polymerized organic binder and filler. It is preferred that the composite material contains fully polymerized organic binder. In particular, the hardness of the composite material can be adjusted by the degree of polymerization. It is possible to manufacture the blank from a not yet fully polymerized composite material and to further polymerize the composite material in a later step, in particular during the production of a dental shaped part.

Mono- or multifunctional (meth)acrylates or a mixture thereof are particularly suitable as polymerizable organic binder. By monofunctional (meth)acrylates are meant compounds with one, by polyfunctional (meth)acrylates compounds with two or more, preferably 2 to 3, polymerizable groups.

Preferred examples are methyl, ethyl, hydroxyethyl, butyl, benzyl, tetrahydrofurfuryl or isobornyl (meth)acrylate, bisphenol-A-di(meth)acrylate, bis-GMA (an addition product of methacrylic acid and bisphenol-A-diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, as well as glycerol dimethacrylate, 1,4-butanediol di(meth)acrylate, 1,10-decanediol di(meth)acrylate or 1,12-dodecanediol di(meth)acrylate. Organic binders which contain at least one radically polymerizable monomer with 2 or more, preferably 2 to 3, radically polymerizable groups are particularly preferred.

Organic or inorganic particulate fillers are preferably suitable as fillers. Preferred inorganic particulate fillers are nanoparticulate fillers based on oxides such as pyrogenic silicic acid or precipitation silicic acid, $ZrO_2$ and $TiO_2$ or mixed oxides of $SiO_2$, $ZrO_2$ and/or $TiO_2$ with an average particle diameter of from 10 to 200 nm, mini fillers such as quartz, glass ceramic or glass powder with an average particle size of from 0.2 to 5 μm and x-ray opaque fillers such as ytterbium trifluoride, nanoparticulate tantalum(V) oxide or barium sulphate. In addition, fibrous fillers such as nanofibres, glass fibres, polyamide or carbon fibres can also be used.

The composite material comprises in particular at least 50 wt.-% and preferably 50 to 90 wt.-% filler.

Metals and metal alloys can also advantageously be used as materials for the blank according to the invention. Here also, the usual metallic materials which are used for such applications in dental engineering are involved. To be emphasized here as materials are (pure) titanium, titanium alloys, for example with added aluminium and vanadium, and cobalt-chromium (CoCr) alloys.

It is further possible for the blank according to the invention to be manufactured from glass or glass ceramic. By "glass" is meant, as is well-known, an amorphous, non-crystalline solid. It is an amorphous substance which can be described thermodynamically as frozen, supercooled liquid. Here, according to the invention for example oxidic glasses, in particular boron silicate glasses, aluminosilicate glasses or lithium silicate glasses, can be used.

Glass ceramics are materials which have also crystalline portions within a glass matrix. Such materials are also used extensively in dental engineering.

In a preferred embodiment, the blank according to the invention consists of a lithium silicate glass ceramic and in particular of a lithium metasilicate or a lithium disilicate glass ceramic.

Ceramic materials from which the blank according to the invention can likewise advantageously be manufactured are polycrystalline materials of which in turn the oxide ceramics and the silicate ceramics are to be emphasized. The oxide ceramics are particularly suitable as starting material for the blanks according to the invention.

By "oxide ceramic" or "oxide ceramics" are meant, to distinguish them from "silicate ceramics", dental ceramics of a specific composition. Oxide ceramics are based on simple oxides of metals, wherein the main representatives of this material group are the oxide ceramics based on aluminium oxide ($Al_2O_3$), zirconium dioxide ($ZrO_2$), titanium dioxide ($TiO_2$) and magnesium oxide (MgO). For all oxide ceramics, the crystalline phase is primarily dominant, with the result that the amorphous glass phase portion of these materials is negligible. The most important representatives are the oxide ceramics based on zirconium dioxide.

It is advantageous if the zirconium dioxide is modified by the addition of other metal oxides. Through the addition of such metal oxides, the high-temperature modification of the pure zirconium dioxide is also stabilized at lower temperatures. Suitable metal oxides are for example calcium oxide (CaO), magnesium oxide (MgO), cerium oxide (CeO, $Ce_2O_3$) or in particular yttrium oxide ($Y_2O_3$). A distinction is drawn between fully stabilized zirconia (FSZ) and partly stabilized zirconia (PSZ). The partly stabilized, polycrystalline, tetragonal zirconium dioxide (TZP—tetragonal zirconia polycrystal) is to be particularly emphasized. Y-TZP means the corresponding stabilization based on yttrium oxide.

A zirconium dioxide ceramic particularly suitable for the invention is 3Y-TZP which contains 3 mol-% yttrium oxide. Hafnium oxide ($HfO_2$) and aluminium oxide ($Al_2O_3$) as natural companions of zirconium dioxide ($ZrO_2$) are likewise contained in small amounts, for example hafnium oxide≤5% and aluminium oxide≤0.5%.

Further preferred zirconium dioxide ceramics which can be used according to the invention are shown in the following table.

| Name of the ingredient | Chemical symbol | Portion in % |
|---|---|---|
| yttrium oxide | $Y_2O_3$ | >4.5 to ≤6.0 |
| hafnium oxide | $HfO_2$ | ≤5.0 |
| aluminium oxide | $Al_2O_3$ | ≤0.5 |
| other oxides | | ≤0.5 |
| zirconium oxide + hafnium oxide + yttrium oxide | $ZrO_2$, $HfO_2$, $Y_2O_3$ | ≥99.0 |

Also suitable as oxide ceramics for the present invention are mixed oxide ceramics based on the main components aluminium oxide ($Al_2O_3$) and zirconium dioxide ($ZrO_2$). Typically, these are mixed oxide ceramics with 80% to 90% aluminium oxide, remainder zirconium dioxide or with about 80% zirconium dioxide, remainder aluminium oxide. Materials with aluminium oxide as main component are called ZTA (zirconia toughened alumina) or ATZ (alumina toughened zirconia).

The ceramic material which is used for the manufacture of the blanks according to the invention can be on the one hand an unsintered, i.e. not sintered, ceramic material or an (only) partially sintered, i.e. not finally-sintered or not densely-sintered, ceramic material.

Such materials are still porous to a greater or lesser extent, but more easily machinable than finally-sintered (densely-sintered) ceramic materials.

On the other hand, the blanks according to the invention can also consist of finally-sintered, i.e. densely-sintered, ceramic material which has only a low residual porosity. As a rule, such materials are harder and thus more difficult to be machined. As a result of the measure of providing preforms in the blank, however, here also the processing times during the production of dental shaped parts are significantly reduced.

Naturally, the above statements regarding unsintered, partially sintered and finally-sintered material also apply accordingly to glass and glass ceramic as materials for the blank. Here also the composition and porosity of the materials can be changed by at least one sintering step, with the result that here also materials with different porosities and thus degrees of hardness can be used as starting materials for the blank according to the invention.

Finally, it may also be mentioned that the blank according to the invention can also be coloured with the help of colour additives. Corresponding colouring techniques are known to a person skilled in the art. As a rule, the colouring of the materials, for example the oxide ceramics used, is carried out with metal atoms or metal ions, wherein in particular metal atoms or metal ions of the rare-earth elements or of the subgroup elements of the periodic table of the elements are used.

The whole blank can be coloured uniformly in one colour or in one colour shade. However, it is also possible to provide different colour layers or to colour the blank with a colour gradient, wherein the colour then changes starting from a starting colour to a final colour without colour leaps.

The process according to the invention for producing the blank according to the invention is characterized in that at least one preform of a dental shaped part is formed in the blank, wherein this preform is then available for producing this shaped part.

In a preferred embodiment, the process according to the invention is characterized in that the blank is produced by machining of the selected material and in particular by injection moulding or extrusion of the selected material. In particular, blanks made of ceramic materials can also be produced by injection moulding and extrusion.

The extrusion allows the production of strands of blanks with a uniform size and arrangement of the preforms. By cutting these strands to the desired thickness, a plurality of blanks, in particular in the form of disks, can be produced in a very economical way. The sintering shrinkage that occurs during a subsequent thermal treatment, e.g. a pre-sintering, is taken into account accordingly.

The process according to the invention for producing dental prostheses (dental shaped parts) is characterized in that the dental shaped part is prepared from the described blank with the preforms, which dental shaped part is specified by the preform, in particular by machining, such as cutting, sawing, grinding, drilling and/or in particular milling.

It is preferred that in the process
(a) dental shaped parts made of different materials are manufactured from blanks made of different materials, and
(b) the dental shaped parts made of different materials are joined together in order to produce multi-sectional dental prostheses.

The dental shaped parts made of different materials are in particular frameworks for dental prostheses and veneers for the frameworks. The frameworks are preferably manufactured from oxide ceramic, metal or metal alloy. The veneers are preferably manufactured from glass ceramic or composite material.

The dental shaped parts made of different materials are joined together in particular by means of a glass solder, a dental cement or an adhesive.

In this way, multi-sectional dental restorations, such as frameworks with veneer, can be easily produced from blanks made of different materials.

Finally, the invention also relates to the use of the blank according to the invention for producing dental prostheses.

Further features of the invention follow from the subsequent example in conjunction with the drawings and the subclaims. Here, the individual features can each be realized alone, or several features can be combined with each other in one embodiment of the invention.

There are shown in the drawings:
FIG. 1a the schematic representation of a blank according to the invention with 13 preforms in top view, and
FIG. 1b the schematic representation of a preform in the blank according to FIG. 1a.

The blank 1 according to the invention according to FIG. 1a has the shape of a disk 2 which has a circumferential groove 3 on its outer circumference. This groove 3 serves to fix and hold the blank 1 in a processing machine during the production of dental shaped parts from this blank.

FIG. 1a shows in top view that the blank 1 has a total of thirteen preforms 4 for single crowns. Of these thirteen preforms, ten are provided in an outer ring in the blank 1. Three further preforms 4 are located in the central part of the blank 1.

All preforms 4 are machined from the solid material of the disk 2, wherein the circumferential line provided with the reference number 5 delimits as processing edge in each case the part of the disk 2 which was processed for the respective preform 4.

The respective preform 4 is connected to the remaining residual material of the disk 2 via a bar 6 which has a circular cross-sectional surface according to FIG. 1a. Accordingly, there is no further material of the disk 2 between the outer circumference of the preform 4 and the processing edge 5 of the corresponding preform 4. The preform 4 is connected to the residual material of the disk exclusively via the bar 6.

Figure 1B:
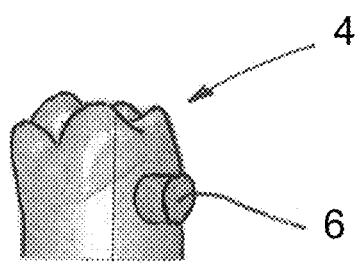

FIG. 1b shows a single preform 4 with bar 6 which is removed from the blank 1 or the disk 2 according to FIG. 1a to illustrate the invention.

FIG. 1b clearly discloses the contour of a single crown for the preform 4. Accordingly, only a relatively small volume of the preform 4 need still be processed in order to arrive at the final dental shaped part, here the single crown. The final shape of the crown is machined from the preform 4 according to the data of the desired crown shape stored in the processing tool. This crown can then be removed from the blank 1 by cutting the bar 6.

EXAMPLE

Firstly, a discoidal blank made of oxide ceramic (3Y-TZB) is prepared. This is a circular disk with a diameter of 98 mm and a thickness (height) of 10 mm. The ceramic material is pre-sintered By means of a CAD/CAM milling station, thirteen preforms for single crowns are machined from this blank, as is shown in FIG. 1a. In this way, the easier production of thirteen single crowns from these preforms is made possible.

An individual single crown can then be produced from each preform according to the corresponding specifications. This is likewise carried out by processing in a milling station, wherein the data for the corresponding crown is calculated from the impression of the situation in the mouth of the patient, taking into account the sintering shrinkage.

After the production of the crown, the latter is densely-sintered, optionally after a finishing.

The invention claimed is:
1. A blank for producing dental shaped parts,
wherein the blank comprises a plurality of preforms of dental shaped parts,
wherein the preforms are each connected to the blank by at least one bar or comparable bridge element,
wherein the preforms are available for producing these dental shaped parts and subsequently cutting the at least one bar or comparable bridge element,
wherein the blank is in the shape of a substantially circular disk with a diameter of more than 20 mm and has at least one holding means provided on an outer circumference of the blank for clamping the blank during the production of the dental shaped parts, and
wherein the blank consists of a metal or a metal alloy, a glass or a glass-ceramic, an unsintered or a partially sintered ceramic, or a densely-sintered ceramic.
2. The blank according to claim 1, wherein the preforms are prepared by machining.
3. The blank according to claim 2, wherein machining comprises at least one of cutting, sawing, grinding, drilling and milling.
4. The blank according to claim 1, wherein one or more of the plurality of preforms is a preform for a single crown.
5. The blank according to claim 1, wherein the thickness of the disk is more than 5 mm.
6. The blank according to claim 1, wherein the dental shaped parts comprise crowns, bridges, veneers, or abutments.
7. The blank according to claim 1, wherein the plurality of preforms comprises more than five or more than 10 preforms.
8. The blank according to claim 1, wherein the diameter is more than 50 mm.
9. The blank according to claim 1, wherein the diameter is more than 80 mm.
10. The blank according to claim 1, wherein the metal or metal alloy is pure titanium, a titanium alloy or a cobalt-chromium (CoCr) alloy.
11. The blank according to claim 1, wherein the ceramic comprises an oxide ceramic.
12. The blank according to claim 11, wherein the oxide ceramic comprises a zirconium oxide ceramic stabilized with yttrium oxide.
13. The blank according to claim 1, wherein the densely-sintered ceramic comprises oxide ceramic.
14. The blank according to claim 13, wherein the oxide ceramic comprises a zirconium oxide ceramic stabilized with yttrium oxide.
15. The blank according to claim 1, wherein the thickness of the disk is between 5 mm and 30 mm.
16. The blank according to claim 1, wherein a dimension or shape of the preforms is approximated or adapted to a dimension or shape of the dental shaped parts that are to be produced.
17. A process for producing a blank for the production of dental shaped parts comprising
forming a blank in the shape of a substantially circular disk with a diameter of more than 20 mm and at least one holding means provided on an outer circumference of the blank for clamping the blank during the production of the dental shaped parts and forming in the blank a plurality of preforms in the shape of dental shaped parts,
wherein the preforms are each connected to the blank by at least one bar or comparable bridge element, and
wherein the preforms are available for producing the dental shaped parts, and subsequently cutting the at least one bar or comparable bridge element, and
wherein the blank consists of a metal or a metal alloy, a glass or a glass ceramic, an unsintered or a partially sintered ceramic, or a densely-sintered ceramic.
18. The process according to claim 17, wherein the blank is produced by machining, injection molding, or extrusion of a selected material.
19. The process for producing the blank according claim 17, wherein at least one preform of a dental shaped part is machined from a discoidal blank, wherein the preform is available for producing the shaped part.
20. The process according to claim 17, which process comprises shaping the blank to provide a plurality of three-dimensional bodies having dimensions or shapes that are approximated to a dimension or shape of the dental shaped parts that are to be produced.
21. A process for producing dental prostheses or dental shaped parts comprising
manufacturing the dental prostheses or dental shaped parts from a blank comprising a plurality of preforms of dental shaped parts, wherein the preforms are each connected to the blank by at least one bar or comparable bridge element, and wherein the preforms are available for producing the dental shaped parts and subsequently cutting the at least one bar or comparable bridge element, and wherein the blank is in the shape of a substantially circular disk with a diameter of more than 20 mm and has at least one holding means provided on an outer circumference of the blank for clamping the blank during the production of the dental prostheses or dental shaped parts, wherein the blank consists of a metal or a metal alloy, a glass or a glass ceramic, an unsintered or a partially sintered ceramic, or a densely-sintered ceramic.

22. The process according to claim 21, in which
  (a) dental shaped parts made of different materials are manufactured from blanks made of different materials, and
  (b) the dental shaped parts made of different materials are joined together in order to produce multi-sectional dental prostheses.

23. The process according to claim 22, in which the dental shaped parts made of different materials comprise frameworks for dental prostheses and veneers for the frameworks.

24. The process according to claim 23, wherein the frameworks are manufactured from oxide ceramic, metal or metal alloy.

25. The process according to claim 23, wherein the veneers are manufactured from glass ceramic or composite material.

26. The process according to claim 21, wherein the dental shaped parts comprise crowns, bridges, veneers, or abutments.

27. A process of using a blank for producing dental prostheses comprising providing a blank consisting of a metal or a metal alloy, a glass or a glass ceramic, an unsintered or a partially sintered ceramic, or a densely-sintered ceramic, and comprising a plurality of preforms of dental shaped parts, wherein the preforms are each connected to the blank by at least one bar or comparable bridge element and are available for producing the dental prostheses, and wherein the blank is in the shape of a substantially circular disk with a diameter of more than 20 mm and has at least one holding means provided on an outer circumference of the blank for clamping the blank during the production of the dental prostheses, machining a plurality of preforms to produce the dental prostheses, and cutting the at least one bar or comparable bridge element after the step of machining the plurality of preforms to produce the dental prostheses.

* * * * *